United States Patent [19]

Monkovic et al.

[11] 3,980,641

[45] Sept. 14, 1976

[54] PROCESS FOR THE PREPARATION OF 14-HYDROXYMORPHINANS

[75] Inventors: Ivo Monkovic; Henry Wong; Gary Lim, all of Candiac, Canada

[73] Assignee: Bristol-Myers Company, New York, N.Y.

[22] Filed: July 31, 1975

[21] Appl. No.: 600,702

[52] U.S. Cl. .......................... 260/240 F; 260/285; 260/326.11 R; 260/566 R; 260/566 F; 260/570.5 CA; 260/590 FA; 260/613 R
[51] Int. Cl.² .................................. C07D 209/44
[58] Field of Search .............. 260/326.11 R, 240 F, 260/240 AL, 240 R, 240 G, 240 A

[56] References Cited
UNITED STATES PATENTS

| 3,166,599 | 1/1965 | Sawa et al. | 260/285 |
| 3,775,414 | 11/1973 | Monkovic et al. | 260/285 |
| 3,819,635 | 6/1974 | Pachter et al. | 260/285 |

FOREIGN PATENTS OR APPLICATIONS

| 1,028,407 | 5/1966 | United Kingdom | 260/285 |

OTHER PUBLICATIONS

Sawa et al., *Tetrahedron,* vol. 24, pp. 6185–6196 (1968).

*Primary Examiner*—Lewis Gotts
*Assistant Examiner*—S. P. Williams
*Attorney, Agent, or Firm*—Robert E. Havranek

[57] ABSTRACT

N-substituted-14-hydroxy-3-substituted-morphinan derivatives have been found to possess potent narcotic agonist or antagonist activity. In particular, the compound 3,14-dihydroxy-N-cyclopropylmethylmorphinan has been found to possess potent agonist-antagonist activity. A new and more efficient total synthesis for the preparation of these compounds is described herein, which improvement comprises using a Schiff base of 4a-(2-aminoethyl)-1,2,3,4,4a,9-hexahydro-6-methoxyphenanthrene to produce 3-methoxy-9-bromo-norhasubanan hydrobromide in substantially improved yields through the intermediate of the formula

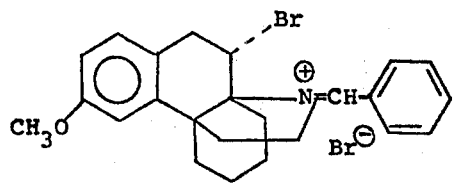

3 Claims, No Drawings

PROCESS FOR THE PREPARATION OF 14-HYDROXYMORPHINANS

BACKGROUND OF THE INVENTION

1. Field of the invention:

This invention embodies a new and novel process for the preparation of analgesics and/or narcotic antagonists.

2. Description of the prior art:

A. (−)-14-hydroxy-3-methoxy-N-methylmorphinan and derivatives thereof have been described by Y. K. Sawa and H. Tada in Tetrahedron, 24, pp. 6185–6196. This paper reports the compound 14-hydroxy-3-methoxy-N-methylmorphinan as being prepared from 14-hydroxydehydrothebainone, an opium alkaloid.

B. U.S. Pat. No. 3,166,599 disclosed compounds having the generic formula

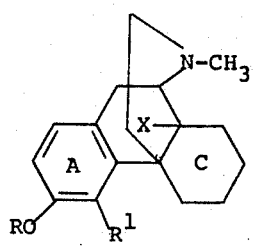

A and

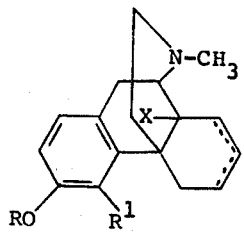

B in which R represents a hydrogen atom or a (lower)-alkyl group (e.g., methyl, ethyl, propyl), $R^1$ represents a hydrogen atom, an aryloxy group (e.g., phenyloxy, naphthyloxy) or a substituted phenyloxy, substituted naphthyloxy wherein the substituent is (lower)alkyl (e.g., methyl, ethyl, propyl), (lower)alkoxy, (e.g., methoxy, ethoxy, propoxy), nitro or amino, X represents a hydrogen atom or a hydroxyl group and, in Formula I, one or two double bond(s) exist(s) in the C ring.

C. British Pat. No. 1,028,407 discloses compounds having the generic formula

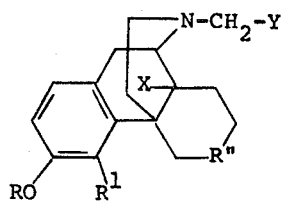

C wherein R represents an alkyl group having not more than five carbon atoms (e.g., methyl, ethyl, propyl), $R^1$ represents a hydrogen atom or an aryloxy group (e.g., phenyloxy or naphthyloxy), R'' represents a methylene group, a carbonyl group or a ketalated carbonyl group (e.g., ethylenedioxymethylene or diethoxymethylene), X represents a hydrogen atom or hydroxyl group and Y represents an alkyl group having not more than five carbon atoms (e.g., methyl, ethyl or propyl), an aryl group (e.g., phenyl or naphthyl) or an aralkyl group in which the alkyl moiety has not more than five carbon atoms (e.g., benzyl or phenethyl) and shows various pharmacological activities such as analgesic activity, antitussive activity and anti-inflammatory activity.

D. U.S. Pat. No. 3,775,414 discloses or claims a process for the preparation of the identical compounds to which this patent application is directed. Claim 1 of that patent is as follows:

The process for the preparation of compounds having the formula

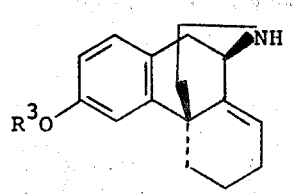

XIa in which $R^3$ is (lower)alkyl, which process comprises the consecutive steps of A. brominating the compound having the formula

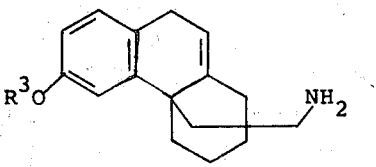

Va in which $R^3$ is (lower)alkyl, with liquid bromine in chloroform, carbon tetrachloride, benzene, toluene, xylene or methylene chloride in a ratio of about 1 mole of bromine per mole of compound Va, at about −15°C. to about +45°C., with stirring to produce the compound having the formula

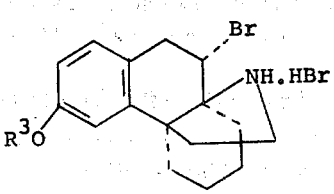

VIa in which $R^3$ is (lower)alkyl; and

B. heating Compound VIa in the presence of anhydrous sodium or potassium bicarbonate in dimethylformamide, benzene, dimethylacetamide, toluene, xylene, dioxane or tetrahydrofuran, in a ratio of no more than 1 mole of bicarbonate per mole of Compound VIa to produce Compound XIa.

E. U.S. Pat. No. 3,819,635 discloses and claims the compounds having the formula

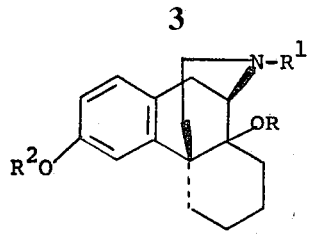

wherein R¹ is selected from the group comprising

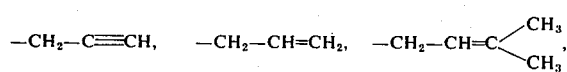

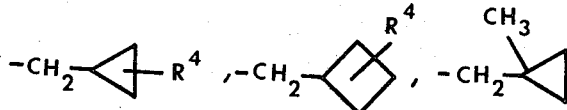

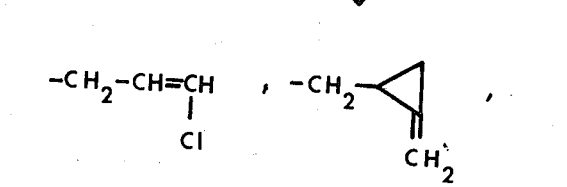

and (lower)alkenyl in which $R^4$ is H or $CH_3$, $R^2$ is selected from the group comprising H, (lower)alkyl,

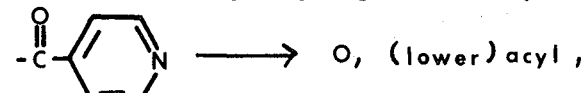

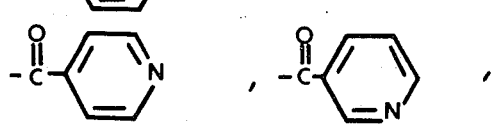

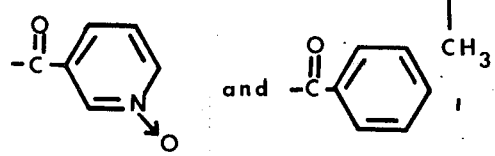

R is H, (lower)acyl, trichloroacetyl or cinnamoyl; or a pharmaceutically acceptable acid addition salt thereof and a process for their preparation which differs from that taught in reference E supra and that claimed in this invention.

SUMMARY OF THE INVENTION

This invention relates to the process for the preparation of compounds having the formula

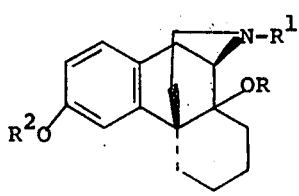

wherein R¹ is selected from the group comprising $-CH_2-C\equiv CH$, $-CH_2-CH=CH_2$, $-CH_2-CH=C\diagup^{CH_3}_{CH_3}$,

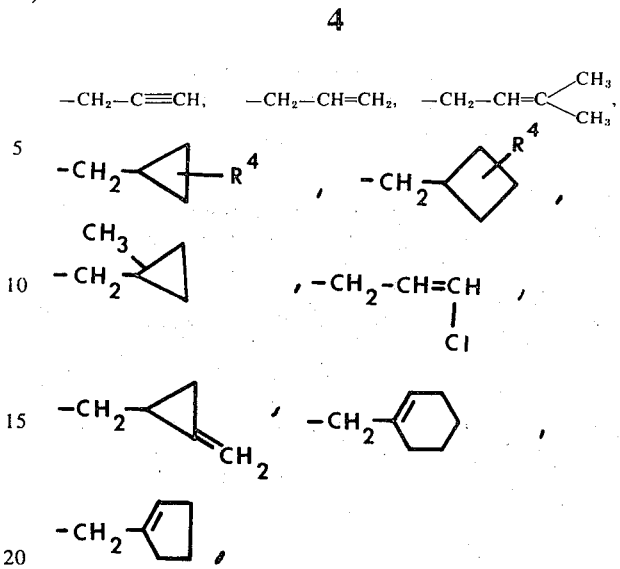

and (lower)alkenyl in which $R^4$ is H or $CH_3$, $R^2$ is selected from the group comprising H, (lower)alkyl, R is H, (lower)acyl, trichloroacetyl or cinnamoyl; or a pharmaceutically acceptable acid addition salt thereof which are prepared from 7-methoxy-3,4-dihydro-1[2H]naphthalenone, the improvement of which is the formation of the intermediate, 3-methoxy-9-bromonorhasubanan hydrobromide, from a Schiff base derivative of 4a-(2-aminoethyl)-1,2,3,4,4a,9-hexahydro-6-methoxyphenanthrene in substantially improved yields.

DISCLOSURE OF THE INVENTION

This invention relates to the total synthesis of N-substituted-14-hydroxy-3-substituted morphinan derivatives having the formula

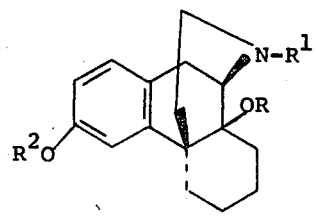

wherein R¹ is selected from the group comprising $-CH_2-C\equiv CH$, $-CH_2-CH=CH_2$, $-CH_2-C=CH\diagup^{CH_3}_{CH_3}$,

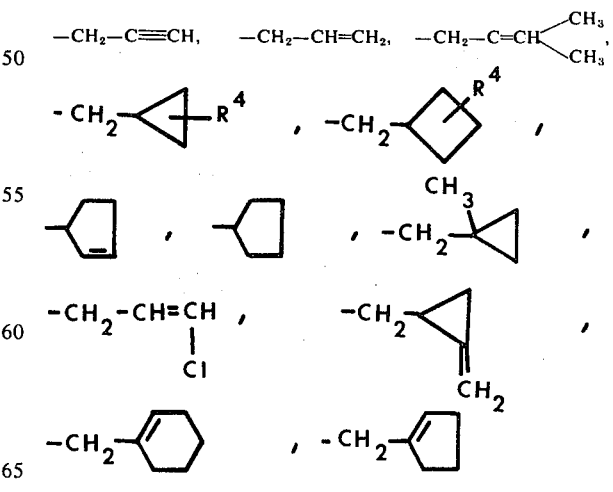

and (lower)alkenyl in which $R^4$ is H or $CH_3$, $R^2$ is selected from the group comprising H, (lower)alkyl,

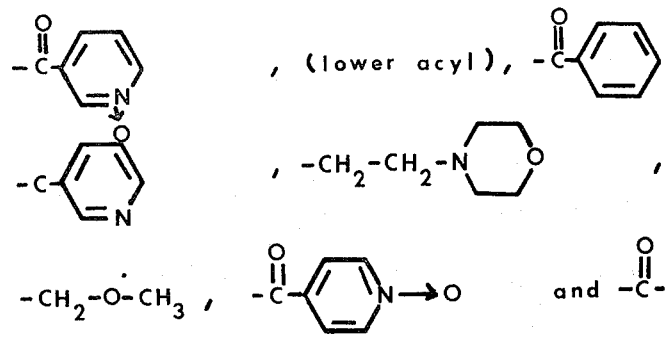 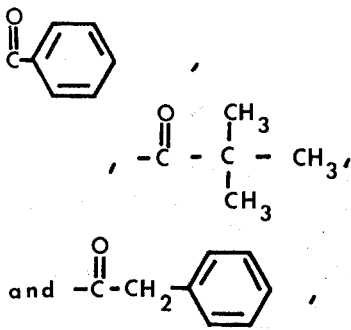

R is H, (lower)acyl, trichloroacetyl or cinnamoyl; or a pharmaceutically acceptable acid addition salt thereof.

Drug abuse by thrill-seeking youth or by people looking for an escape from the realities of everyday life has become more and more common place in our present society. One class of widely abused drugs are the narcotic analgetics such as codeine, morphine, meperidine, etc. It is because of the high addictive potential of these agents that much time and money are being expended by the pharmaceutical industry and by governments to try and discover and develop new non-addicting analgetics and/or narcotic antagonists.

It was an object of the present invention to develop a method of synthesis for the above-described Compounds (I) that would not be dependent upon opium alkaloids as starting materials and yet would be commercially feasible.

The objectives of the present invention have been achieved by the process of preparing the compounds of Formula I by their total synthesis from the readily available starting material 7-methoxy-3,4-dihydro-1-[2H]-naphthalenone.

The compounds of the instant invention have the basic morphinan nucleus which is numbered and represented by the following plane formula:

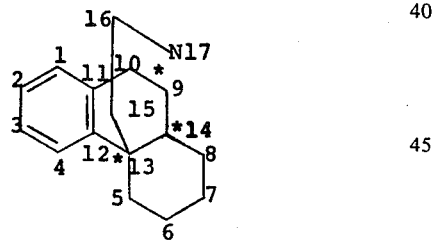

Although there are three asymetric carbons (asterisks) in the morphinan molecule, only two diastereoisomeric (racemic) forms are possible, because the iminoethano system, attached to position 9 and 13, is geometrically contained to a cis(1,3-diaxial)-fusion. These racemates can therefore differ only at the junction of rings B and C—in other words, in the configuration of carbon 14. The only variable will be the cis and trans relationship between the 5 (13) and 8 (14) bonds (Analgetics, Ed. George de Stevens, Academic Press, New York, p. 137 (1965)).

When in the compounds of the present invention, the 5 (13) and 8 (14) bonds are trans to each other, we have compounds commonly designated as "isomorphinans". On the other hand, when 5 (13) and 8 (14) are cis to each other, we have compounds commonly designated as "morphinans". The use of graphic representation of a "morphinan" or "isomorphinan" is meant to include the dl racemic mixture and the resolved d and l isomers thereof.

The "isomorphinans" disclosed and claimed herein are primarily useful as intermediates in the preparation of the biologically potent analgetic and/or narcotic antagonist agent of the present invention.

In addition, the "isomorphinan" and "morphinan" compounds of the present invention can each exist as two optical isomers, the levorotatory and dextrorotatory isomers. The optical isomers can be graphically illustrated as:

MORPHINANS

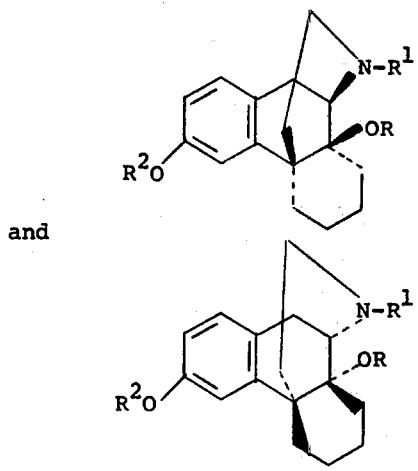

and

ISOMORPHINANS

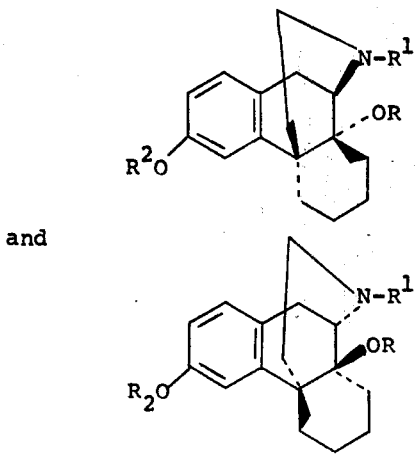

The present invention embodies all of the morphinan isomers including the optical isomers in their resolved form.

The optical isomers can be separated and isolated by fractional crystallization of the diastereoisomeric salts formed, for instance, with d- or l-tartaric acid or D-(+)-α-bromocamphor sulfonic acid. The levorotatory isomers of the compounds of the present invention are the most preferred embodiments.

For the purpose of this disclosure, the term "(lower-)alkyl" is defined as an alkyl radical containing 1 to 6 carbon atoms. "(Lower)alkenyl" is defined as a hydrocarbon radical of 3 to 7 carbons containing one double bond. The term "(lower)acyl" is an acyl radical of 2 to 6 carbon atoms, e.g., acetyl, propionyl, isobutyryl, etc. The term "pharmaceutically acceptable acid addition salt" is defined to include all those inorganic and organic acid salts of the compounds of the instant invention, which salts are commonly used to produce nontoxic salts of medicinal agents containing amine functions. Illustrative examples would be those salts formed by mixing the compounds of Formula I with hydrochloric, sulfuric, nitric, phosphoric, phosphorous, hydrobromic, maleic, malic, ascorbic, citric or tartaric, pamoic, lauric, stearic, palmitic, oleic, myristic, lauryl sulfuric, naphthalenesulfonic, linoleic or linolenic acid, and the like.

The compounds of the instant invention are prepared by a total synthesis comprising at least 11 steps. The synthesis is efficient and is commercially feasible. The process is outlined in Charts I, II and III.

CHART I

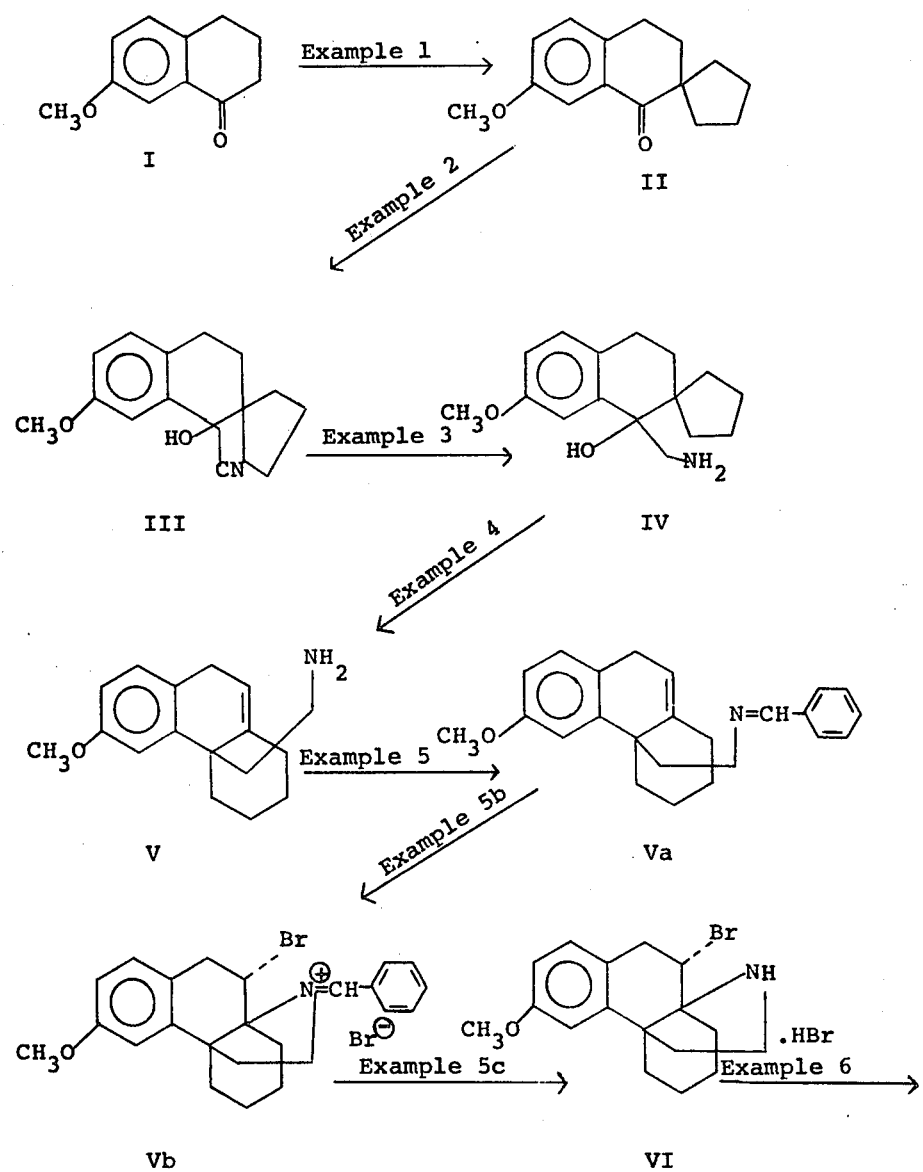

CHART I -continued
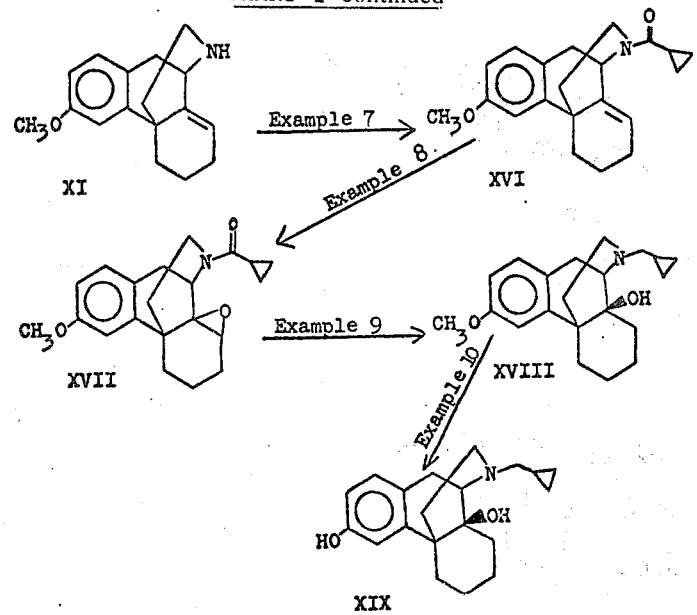
CHART II
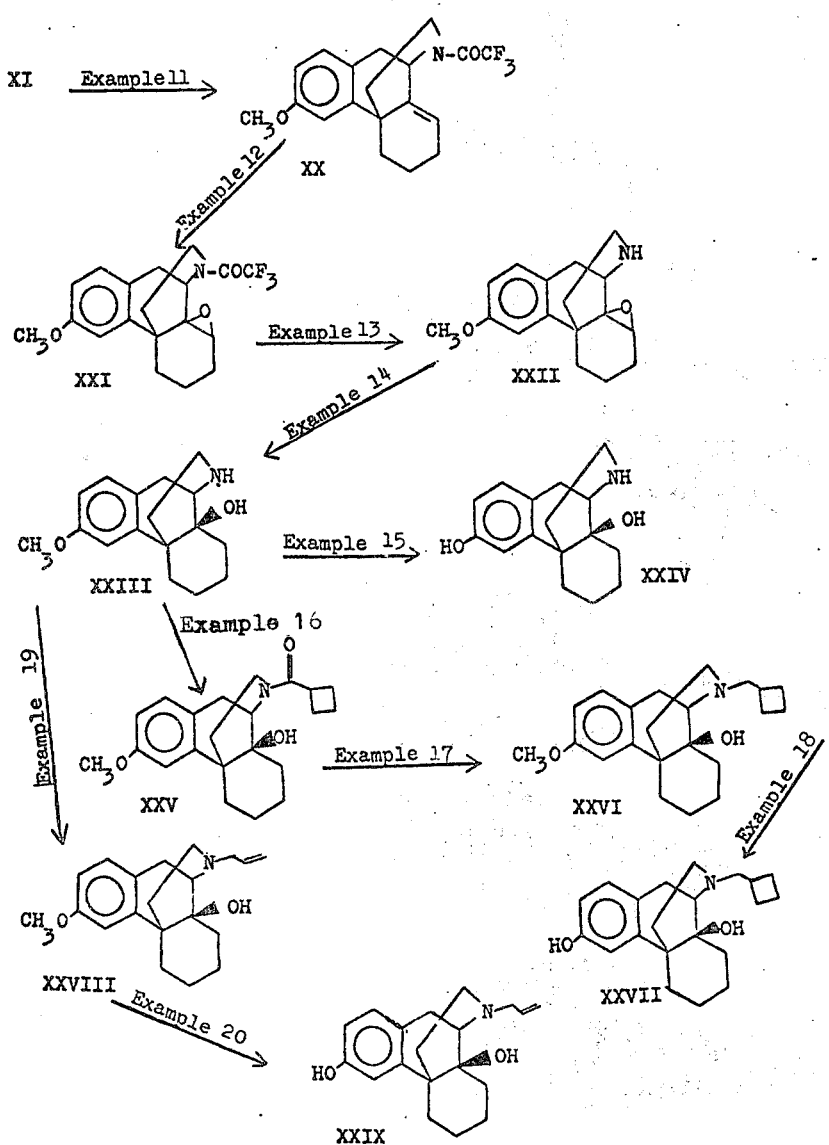

CHART III
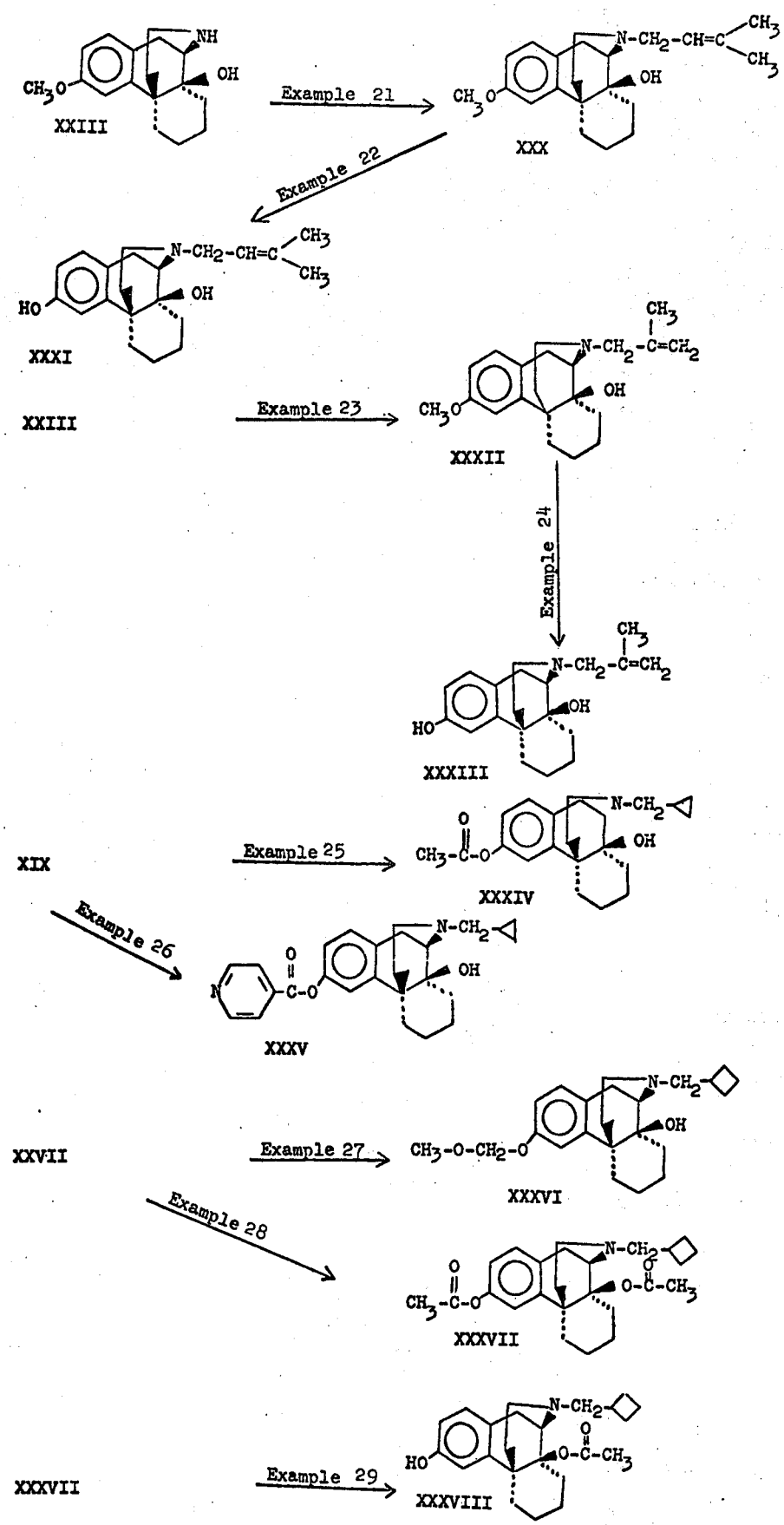

For the purpose of this disclosure the term "inert organic solvent" means an organic solvent that does not participate in the reaction to the extent that it emerges unchanged from the reaction. Such solvents are methylene chloride, chloroform, dichloroethane, tetrachloromethane, benzene, toluene, ether, ethyl acetate, xylene, tetrahydrofuran, dioxane, dimethylacetamide, and the like when an acid halide is employed. When an alkylation reaction is being performed, the inert solvent used may also include (lower)alkanols such as methanol, ethanol, n-propanol, isopropanol and the like. The term "organic tertiary amine" means a tertiary amine commonly employed as a proton acceptor in alkylation and acylation reactions. Such amines are tri(lower)alkylamines, e.g., trimethylamine, triethylamine, and the like, pyridine, dimethylaniline, N-methylpiperidine, and the like.

A preferred embodiment of the present invention is the process for the preparation of compounds having the formula

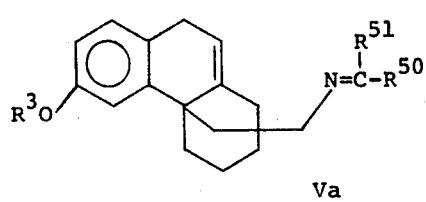

VI in which $R^3$ is (lower)alkyl, which process comprises the consecutive steps of A. treating the compound having the formula

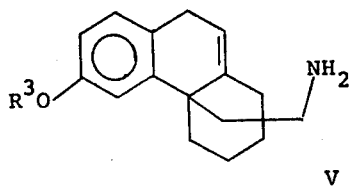

V in which $R^3$ is (lower)alkyl with an aldehyde or ketone capable of forming a Schiff base to produce the compound having the formula

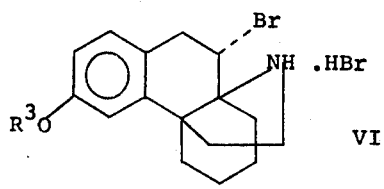

Va in which $R^{50}$ and $R^{51}$ are the residue of the aldehyde or ketone;

B. brominating compound Va with liquid bromine in chloroform, carbon tetrachloride, benzene, toluene, xylene or methylene chloride in a ratio of about 1 mole of bromine per mole of Compound Va, at about −15°C. to +45°C., with stirring to produce the compound having the formula

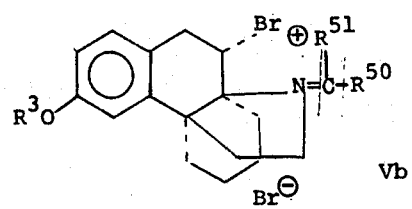

Vb in which $R^3$ is (lower)alkyl and $R^{51}$ and $R^{50}$ are as above;

C. heating compound Vb with water and toluene or benzene to produce compound VI.

Another preferred embodiment is the process of producing compound VI which comprises the consecutive steps of A. treating compound V with a ketone or aldehyde capable of forming a Schiff base and having the formula

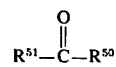

in which $R^{50}$ is (lower)alkyl or a moiety having the formula

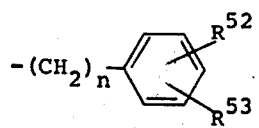

in which $n$ is 0 to 5 inclusive, $R^{52}$ and $R^{53}$ are alike or different and each is H, $NO_2$, Cl, OH, bromo, fluoro, (lower)alkyl or (lower)alkoxy; $R^{51}$ is H, (lower)alkyl or an aralkyl group having the formula

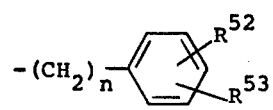

in which n is an integer of 1 to 5 and $R^{52}$ and $R^{53}$ are as defined above; to produce the compound having the formula

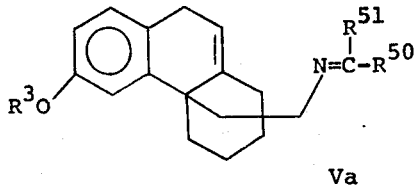

in which $R^3$, $R^{51}$ and $R^{50}$ are as above;

B. brominating compound Va with liquid bromine in chloroform, carbon tetrachloride, benzene, toluene, xylene or methylene chloride in a ratio of about 1 mole of bromine per mole of Compound Va, at about −15°C. to +45°C., with stirring to produce the compound having the formula

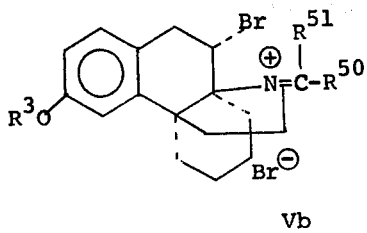

in which $R^3$ is (lower)alkyl and $R^{50}$ and $R^{51}$ are as above;

C. heating compound Vb with water and toluene or benzene to produce compound VI.

A most preferred embodiment is the process of producing compound VI which comprises the consecutive steps of A. heating compound V with benzaldehyde or p-nitrobenzaldehyde in the presence of a reaction inert organic solvent capable of forming an azeotrope selected from the group consisting of benzene, toluene and xylene, to produce the compound having the formula

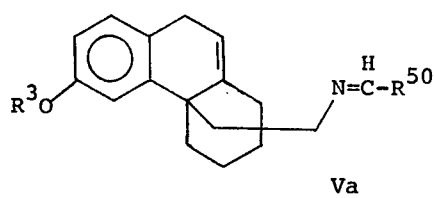

in which $R^{50}$ is

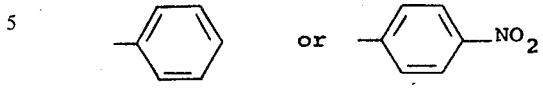

and $R^3$ is defined as above;

B. treating compound Va with bromine in carbon tetrachloride in a ratio of 1 mole of bromine per mole of compound Va, at a temperature of about −5° to +35°C., to produce the compound having the formula

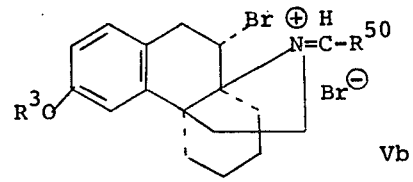

in which $R^3$ and $R^{50}$ are as defined above; and

C. heating compound Vb to reflux in about equal quantities of water and benzene or toluene to produce compound VI.

The essence of the present invention is an improvement in yield of the overall process for the total synthesis of the above-described morphinans. The improvement in yield occurs primarily in the steps of converting compounds V to compound VI via the Schiff base in essentially quantitative yields as compared to the direct conversion of compound V to compound VI without the use of the Schiff base intermediate in 72% yield.

Also a preferred embodiment is the compound having the formula

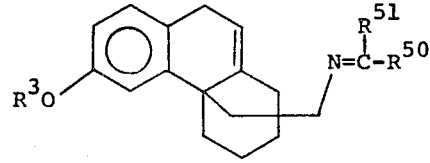

in which $R^3$ is (lower)alkyl, $R^{50}$ is (lower)alkyl or a moiety having the formula

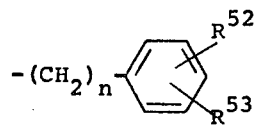

in which n is 0 to 5 inclusive, $R^{52}$ and $R^{53}$ are alike or different and each is H, $NO_2$, Cl, OH, bromo, fluoro, (lower)alkyl, (lower)alkoxy; $R^{51}$ is H, (lower)alkyl or an aralkyl group having the formula

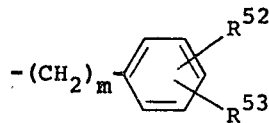

in which n is an integer of 1 to 5 and $R^{52}$ and $R^{53}$ are as defined above.

A more preferred embodiment is the compound having the formula

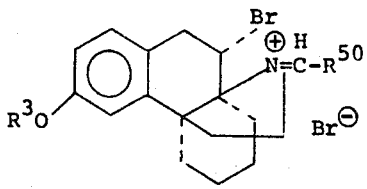

in which $R^3$ is (lower)alkyl and $R^{50}$ is phenyl or p-nitro phenyl.

A most preferred embodiment is the compound having the formula

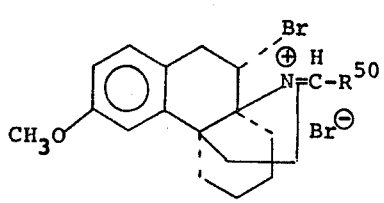

in which $R^{50}$ is phenyl or nitrophenyl.

Another preferred embodiment is the compound having the formula

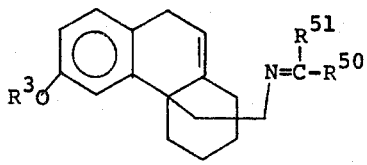

in which $R^3$ is (lower)alkyl, $R^{50}$ is (lower)alkyl or a moiety having the formula

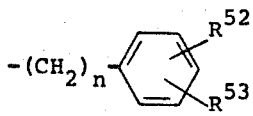

in which n is 0 to 5 inclusive, $R^{52}$ and $R^{53}$ are alike or different and each is H, $NO_2$, Cl, OH, bromo, fluoro, (lower)alkyl or (lower)alkoxy; $R^{51}$ is H, (lower)alkyl or an aralkyl group having the formula

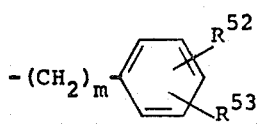

in which n is an integer of 1 to 5 and $R^{52}$ and $R^{53}$ are as defined above.

A more preferred embodiment is the compound having the formula

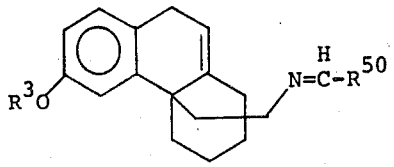

in which $R^3$ is (lower)alkyl and $R^{50}$ is phenyl or p-nitrophenyl.

A most preferred embodiment is the compound having the formula

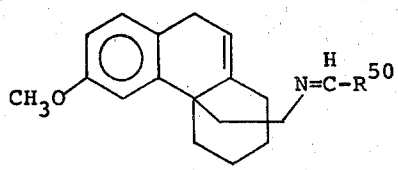

in which $R^{50}$ is phenyl or p-nitrophenyl.

EXPERIMENTAL SECTION

Example 1

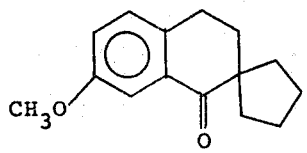

3,4-dihydro-7-methoxy-2,3-tetramethylene-1(2H)-naphthalenone (II)

A nitrogen atmosphere was maintained throughout the following reaction. To a stirred and refluxing suspension of 12 g. (0.5 mole) of sodium hydride in 100 ml. of dry benzene was added during 30 minutes, 16.6 g. (0.2 mole) of anhydrous t-amyl alcohol. The reaction mixture was stirred and refluxed during 15 minutes, and then a solution of 35.2 g. (0.2 mole) of 7-methoxy-3,4-dihydro-1(2H)-naphthalenone (I) in 100 ml. of dry benzene was added dropwise. After another 15 minutes, 54.0 g. (0.25 mole) of 1,4-dibromobutane were added over a period of 15 minutes followed by 100 ml. of dry benzene. The resulting reaction mixture was stirred and refluxed during 50 hours. It was then cooled, washed twice with water, dried over anhydrous sodium sulfate and concentrated at reduced pressure. The residual yellow oil was dissolved in 400 ml. of petroleum ether (B.P. 30°–60°C.), treated with charcoal, filtered and the solvent evaporated. The resulting clear light yellow oil (45.7 g.) was distilled at reduced pressure and the fraction boiling at 120°–123°C./0.05 mm. was collected. This procedure yielded 29.4 g. (65%) of colorless spiro ketone II. The infrared (IR) and nuclear magnetic resonance (NMR) spectra were consistent with the structure.

Anal. Calc'd. for $C_{15}H_{18}O_2$ (percent): C, 78.22; H, 7.88. Found (percent): C, 77.96; H, 7.93.

EXAMPLE 2

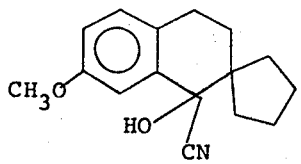

1-hydroxy-7-methoxy-1,2,3,4-tetrahydro-2,2-tetramethylene-1-naphthaleneacetonitrile (III)

To a stirred solution of 13.8 ml. (0.022 mole) of 1.6M n-butyl lithium in hexane at −80°C. under nitrogen was rapidly added 13.8 ml. of anhydrous tetrahydrofuran (THF) followed immediately by a solution of 0.82 g. (0.02 mole) of acetonitrile in 20 ml. THF which was added during 7 minutes. After stirring for 1 hour at −80° C., the resulting white suspension was treated during 5 minutes with a solution of 4.60 g. (0.02 mole) of the spiroketone II in 20 ml. THF. The cold bath was removed and the solution was stirred for 10 minutes before it was poured into ice-water acidified with hydrochloric acid. The layers were separated, and the aqueous layer was extracted with three 25 ml. portions of benzene.

After drying over anhydrous sodium sulfate, evaporation of the solvent and recrystallization of the remaining solid from chloroform, there was obtained 4.4 g. (80%) of white solid III, M.P. 140°–142°C. The IR and NMR spectra were consistent with the structure.

Anal. Calc'd. for $C_{17}H_{21}NO_2$ (percent): C, 75.24; H. 7.80; N, 5.16. Found (percent): C, 75.12; H, 7.91; N, 4.89.

EXAMPLE 3

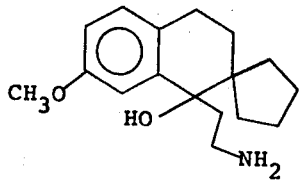

1-(2-aminoethyl)-7-methoxy-1,2,3,4-tetrahydro-2,2-tetramethylene-1-naphthol (IV)

To a stirred suspension of 0.57 g. (0.015 mole) of lithium aluminum hydride in 20 ml. anhydrous tetrahydrofuran (THF) under $N_2$ was added a solution of 2.71 g. (0.01 mole) of III in 20 ml. tetrahydrofuran. The reaction mixture was stirred for 4 hours at room temperature (r.t.). It was then cooled and treated with 0.06 ml. of water, followed by 0.6 ml. of 5 N sodium hydroxide and finally 1.8 ml. of water. The inorganic material was filtered off and washed well with ether. The filtrate was extracted with two portions of 15 ml. of 1 N hydrochloric acid. The extract was basified with aqueous ammonia, and the free base was taken up in ether. After drying over anhydrous sodium sulfate and evaporation of the solvent, there was obtained 2.2 g. of slightly yellow oil IV. It was converted to the oxalate salt in acetone and recrystallized from methanol. This procedure yielded 2.9 g. (76%) of white solid, containing 1 mole of methanol of crystallization; M.P. 178–180.

In another experiment IV was obtained from II without isolation of III as follows:

4.6 g. (0.02 mole) of the spiroketone II in 20 ml. of tetrahydrofuran was converted to the nitrile III according to the procedure described on the preceding page. To the resulting cold solution (=80°C.) of III, was added 1.14 g. (0.03 mole) of lithium aluminum hydride in small portions. After the addition had been completed, the reaction mixture was stirred at r.t. for 4 hours. After work up as above, there was obtained 5.7 g. (75% overall) of the oxalate salt of IV, M.P. 179°–80°C. In both procedures, the IR and NMR spectra were consistent with the desired product.

Anal. Calc'd. for $C_{17}H_{25}NO_2.C_2H$ $O_4$. $CH_3OH$ (percent): C, 63.31; H, 7.70; N, 3.69. Found (percent): C, 63.41; H, 7.43; N, 3.79.

EXAMPLE 4

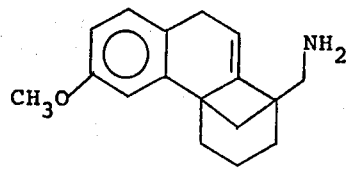

4a-(2-aminoethyl)1,2,3,4,4a,9-hexahydro-6-methoxyphenathrene (V)

METHOD A

Compound IV [1.50 g. (0.00548)] (free base liberated from 2 g. of oxalate salt) in 5 ml. of ether was treated with 1.5 ml. of concentrated HCl under $N_2$ at 55°–60°C. for 5 hours. To the cooled mixture were added in succession 10 ml. of ether and 10 ml. of water. After shaking, the two layers were separated. The acidic layer was made alkaline with aqueous ammonia and extracted with ether. The ether layer was dried ($K_2CO_3$) and concentrated to yield 1.30 g. of pale yellow oil V. It was converted to an oxalate salt in acetone. The crystals were filtered and washed with a small amount of methylene chloride. The IR and NMR spectra were consistent with the structure. Yield 1.7 g. (96%) of white solid, M.P. 187°–13°C.

Anal. Calc'd. for $C_{17}H_{23}NO.C_2H_2O_4$ (percent): C, 65.69; H, 7.25; N, 4.03. Found (percent): C, 64.44; H, 7.47; N, 4.43.

METHOD B 120 g. of the oxalate salt of IV was slurried in 700 ml. of water, and to it was added 400 ml. of benzene and 60 ml. of concentrated ammonia. The mixture was stirred until all the solid had disappeared (ca. 15 minutes) and then the layers were separated. The water layer was extracted with another 100 ml. of benzene, and the combined benzene layers were shaken with 200 ml. of saturated NaCl solution, filtered over $K_2CO_3$ and concentrated in vacuo. The residual oil (ca. 90 g.) was dissolved in 300 ml. of ether in a one l. round-bottom flask and while cooling with an ice-water bath and swirling, to it was added carefully 90 ml. of concentrated HCl and then gently refluxed on the steambath for 3 hours in a closed system using an oil bubbler.

Then the layers were separated, and to the water layer was added 150 ml. of water. After cooling, the solid was filtered off and washed with 50 ml. of acetonitrile to yield 80–85 g. of the HCl salt. From the mother liquor a further crop of the product can be obtained by liberating the free base and repeating HCl treatment as above. The product was recrystallized as the hydrochloride from methanol-ether; M.P. 135° (dec.).

Anal. Calc'd. for $C_{17}H_{23}No.HCl\ CH_3OH$ (percent): C, 66.34; H, 8.66; N, 4.29. Found (percent): C, 66.34; H, 8.02; N, 4.46.

EXAMPLE 5

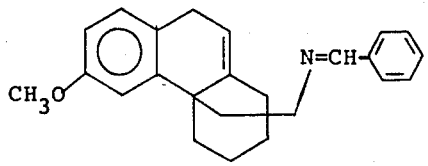

Benzaldehyde Schiff Base of
4a-(2-aminoethyl)-1,2,3,4,4a,9-hexahydro-6-methoxyphenanthrene Va.

4a-(2-Aminoethyl)-1,2,3,4,4a,9-hexahydro-6-methoxyphenanthrene [V, 10.28 g. (40 mmole)] and 4.24 g [40 mmole] of benzaldehyde were mixed together in 50 ml of dry benzene and evaporated to dryness in vacuo with the aid of heat. The residue remaining is the Schiff base title product, Va, in quantitative yield. The oil crystallized from ether, m.p. 99°–101°C.

Anal. Calc'd. for $C_{24}H_{27}NO$: C, 83.44; H, 7.88; N, 4.05. Found: C, 83.55; H, 8.00; N, 4.00.

EXAMPLE 5A

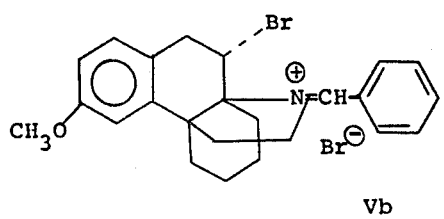

Benzaldehyde Schiff Base of
3-methoxy-9α-bromonorhasubanan hydrobromide Vb.

The Schiff base Va (40 mmole) obtained in Example Va was dissolved in 50 ml of methylene chloride and treated with 40 mmole of $Br_2$ dissolved in carbon tetrachloride (1 mole of bromine dissolved in 1 liter of carbon tetrachloride) at room temperature for about 30 minutes. The solution was concentrated to remove the methylene chloride and carbon tetrachloride. The solid that formed was dissolved in benzene and then evaporated repeatedly to produce a crystalline solid mass identified as the title compound Vb. The solid was used as is in example 5b.

Anal. Calc'd. for $C_{24}H_{27}Br_2NO$: C, 57.05; H, 5.39; N, 2.77. Found: C, 56.99; H, 5.58; N, 3.02

EXAMPLE 5b

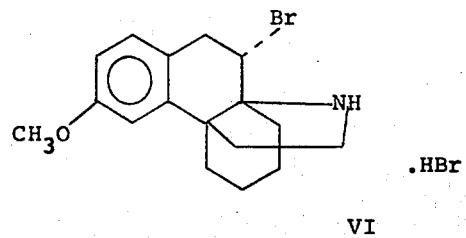

The compound Vb [40 mmole] obtained in example VA was treated with 30 ml of water and 30 ml of toluene and the mixture was heated to reflux for 20 minutes with efficient stirring. The mixture was then cooled and the solid collected by filtration. The solid was washed well with acetone, followed by air drying. The yield of VI from V was essentially quantitative. Crystalline product collected was 14.4 g (86%) of analytical material.

Anal. Calc'd. for $C_{17}H_{22}BrNO.HBr$ (percent): C, 48.94; H, 5.56; N, 3.36; Br, 38.31. Found (percent): C, 48.66; H, 5.43; N, 3.19; Br, 38.29.

EXAMPLE 6

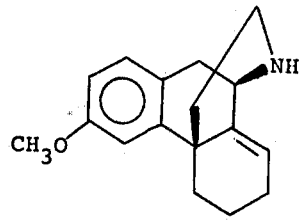

3-methoxy-$\Delta^{8,14}$-morphinan (XI)

Into a 5-liter, one-necked round-bottom flask equipped with a condenser and a magnetic stirrer, was put VI (417.2 g., 1.0 mole), anhydrous sodium bicarbonate (84.0 g., 1.0 mole) and 2000 ml. of reagent grade dimethylformamide.[4] The flask was then placed in a pre-heated oil bath at 130°–135° and the reaction mixture stirred vigorously for 1.5 hours.

[4]The dimethylformamide was dried by adding 20% by volume of benzene and distilling at atmospheric pressure.

The reaction mixture was diluted with 8 liters of saturated brine, alkalized with sodium carbonate solution, and then extracted 4 times with ether. The ether extracts were washed with brine, dried (sodium sulfate), and evaporated in vacuo. This left 255.2 g. of a brown oil.[5]

[5]The NMR spectrum of the oil indicated approximately 70% purity, therefore a 70% yield.

The brown oil was dissolved in 1 liter of dry ether and added to a solution of anhydrous oxalic acid (99 g., 1.1 mole) in 3 liters of dry ether. The resultant precipitate was filtered off and recrystallized from methanol/ether (1:4) to give a white solid, 153 g. (57%), m. 180°–184°.

A second crop of product was obtained by evaporating the above mother liquor to dryness, dissolving the residue in methanol, treating with norite, diluting with dry ether and filtering the resultant solid. 66.6 g., m. 180°–184°. Total yield was 220 g. (61%).

EXAMPLE 7

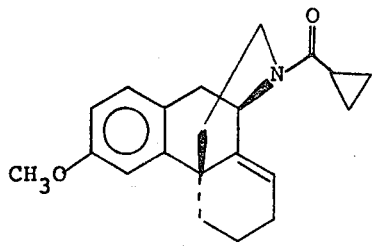

N-cyclopropylcarbonyl-3-methoxy-$\Delta^{8,14}$-morphinan (XVI)

The acid chloride of cyclopropylcarboxylic acid (3.0 g., 28.7 mmole) was added to a cooled and stirred solution of 6.4 (25 mmole) of XI and 2.5 g. (31.3 mmole) of pyridine in 30 ml. of methylene chloride over a period of 10 minutes. After stirring for another 10 minutes, the solution was washed successively with water, 15 ml. of 0.2 n.NaOH, 10 ml. of 1 N HCl, and again with water. After drying over $Na_2SO_4$, the solvent was evaporated and the residue crystallized from 15 ml. of ether. A total of 7.73 g. (95.7%): M.P. 125°–28° C., was obtained. Recrystallization from methanol increased the M.P. to 133°–35°C. The IR and NMR spectra were consistent with the structure.

Anal. Calc'd. for $C_{21}H_{25}NO_2$ (percent): C, 77.98; H, 7.79; N, 4.33. Found (percent): C, 77.86; H, 7.87; N, 4.30.

EXAMPLE 8

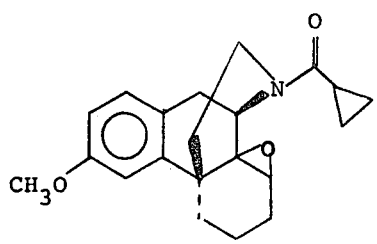

N-cyclopropylcarbonyl-8,14-epoxy-3-methoxymorphinan (XVII)

To a solution of 3.33 g. (10.3 mmole) of XVI in 35 ml. $CH_2Cl_2$ at 0° C. was added 2.31 g. of 85% m-chloroperbenzoic acid (11.3 mmole). The mixture was stirred at 0°–5°C. until all the peracid was dissolved. The mixture was left at room temperature for 6 hours. Work up in usual manner afforded an oil which was dissolved in 10 ml. of ether and left for 24 hours at 5° C. The solid was filtered off to yield 2.3 g. (66%); M.P. 134°–36°C.

Recrystallization from a $CH_2Cl_2$-ether mixture afforded a sample melting at 140°–42°C. The IR and NMR spectra were consistent with the structure.

Anal. Calc'd. for $C_{21}H_{25}NO_3$ (percent): C, 74.31; H, 7.42; N, 4.13. Found (percent): C, 74.13; H, 7.39; N, 4.13.

EXAMPLE 9

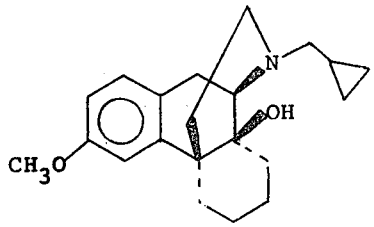

N-cyclopropylmethyl-14-hydroxy-3-methoxymorphinan (XVIII)

To a stirred suspension of 1.8 g of $LiAlH_4$ in 50 ml. of anhydrous THF was added dropwise during 5 minutes a solution of 6.0 g. (17 mmole) of XVII in 10 ml. THF. The mixture was refluxed during one hour and then worked up in the usual manner. The product was dissolved in petroleum ether (B.P. 40°–60°C.) and filtered through celite-charcoal to give 5.73 g. of an oil. Treatment with anhydrous HCl in ether afforded 6.15 g. (95.5%) of the hydrochloride salt, M.P. 223°–25°C. Recrystallization from methanol-ether increased the M.P. to 259°–60°C. The IR and NMR spectra were consistent with the structure.

Anal. Calc'd. for $C_{21}H_{29}NO_2.HCl.1/2H_2O$ (percent): C, 67.67; H, 8.37; N, 3.76. Found (percent): C, 67.70; H, 8.02; N, 3.72.

EXAMPLE 10

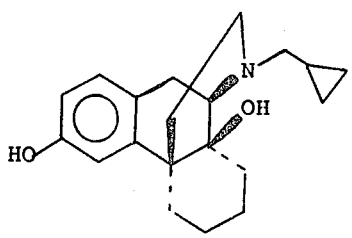

3,14-dihydroxy-N-cyclopropylmethylmorphinan (XIX)

METHOD A

A mixture of 4.1 g. (11.7 mmole) of the hydrochloride salt of XVIII and 13.4 g. of anhydrous pyridine hydrochloride was heated under nitrogen at 187°–95°C. for 1 hour. The cooled mixture was dissolved in 40 ml. of water, basified with aqueous ammonia and extracted with 2 × 40 ml. of ether. Drying and evaporation of the solvent yield 3.0 g. of semi-solid product, which was dissolved in ether. After treatment with charcoal, the product crystallized to yield 2.54 g. (69.4%) of free base M.P. 157°–59° C. The hydrochloride salt, recrystallized from methanolacetone, had a M.P. 179°–81°C. with contraction starting at 163. The product analysed for ½ molecule of methanol of crystallization. The IR and NMR spectra were consistent with the structure.

Anal. calc'd. for $C_{20}H_{27}NO_2.HCl.½CH_3OH$ (percent): C, 67.32; H, 8.37; N, 3.83. Found (percent): C, 67.56; H, 8.20; N, 3.90.

METHOD B

Into a cooled (Dry Ice-acetone) three-l. three-necked flask equipped with a mechanical stirrer, dropping funnel and a gas trap was placed a solution of 133.1 g. (0.5312 mole) of $BBr_3$ in 250 ml. of dry methylene chloride. Then a solution of 58 g. (0.177 mole) of the free base XVIII in 1.2 l. of dry methylene chloride was added dropwise under nitrogen (time=1 hour).

After the addition had been completed, the reaction mixture was stirred in the cold for 1 hour, and then at room temperature for 3 hours.

1. The reaction mixture was cooled (ice-bath) and carefully decomposed with 350 ml. of cold water.
2. It was transferred into a four l. Erlenmeyer flask and treated carefully with 200 ml. of concentrated ammonium hydroxide with cooling and stirring. The layers were separated and the aqueous layer extracted with 200 ml. of methylene chloride. The combined organic extracts were dried (MgSO$_4$) and evaporated, in vacuo, to give an oil in quantitative yield.

The oil was taken up in 250 ml. of reagent acetone, cooled, and treated with 17 ml., of concentrated hydrochloric acid. After standing in the cold for 18 hours, the solid was collected by filtration and washed with 2 × 60 ml. of cold acetone. The product was recrystallized from 90% ethyl alcohol. The IR and NMR spectra were consistent with the structure. Yield: 55.0 g. (86.3%); M.P. 275°–77°C. (dec.).

Anal. Calc'd. for $C_{20}H_{27}NO_2 \cdot HCl$ (percent): C, 68.65; H, 8.07; N, 4.00. Found (percent): C, 68.01; H, 8.17; N, 3.88.

1. During one hour at −70° C. the boron complex hardened and stirring was very difficult. The cold bath was removed and the stirring resumed after softening of the mass. The reaction mixture was then stirred during three hours at room temperature.
2. During the initial stage of decomposition, a violent reaction might occur. Therefore, it was essential to provide vigorous stirring and efficient cooling during the slow addition of water.

EXAMPLE 11

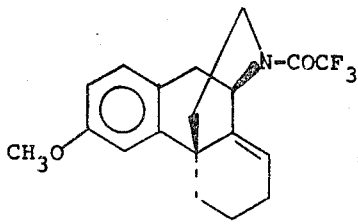

3-methoxy-N-trifluoroacetyl-$\Delta^{8,14}$-morphinan (XX)

To a solution of 55.1 g. (20 mmole) of the secondary amine XI in 60 ml. of dry ether was added 24 g. (280 mmole) of Na$_2$CO$_3$. The mixture was cooled and vigorously stirred, and 32 ml. (228 mmole) of trifluoroacetic anhydride was added at as rapid a rate as possible without the reaction getting out of control. The cooling bath was removed and the vigorous stirring continued for 20 minutes. The reaction mixture was poured into chloroform, the excess anhydride was destroyed with ice, and the chloroform solution was dried and evaporated to give an oil; weight 6.33 g. The oil was covered with 15 ml. of ether and it crystallized on standing. It was filtered to give a solid 4.96 g. (70%) M.P. 94–96%. The IR and NMR were consistent with the structure.

Anal. Calc'd. for $C_{19}H_{20}NO_2$ (percent): C, 64.95; H, 5.74; N, 3.99. Found (percent): C, 65.34; H, 6.76; N, 3.03.

EXAMPLE 12

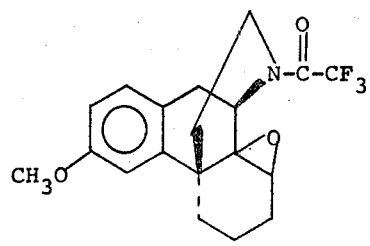

8,14-epoxy-3-methoxy-N-trifluoroacetylmorphinan (XXI)

The procedure is the same as that described for the preparation of Compound VII in Example 6 using the following materials: 3.85 (10.96 mmole) of Compound XX; 2.07 g. (12 mmole) of 85% m-chloroperbenzoic acid; and 30 ml. of methylene chloride. Reaction time; 6 hours.

After the usual work up, the residual oil was covered with 5 ml. of ether. Crystals formed which were collected by filtration. An analytical sample was prepared by recrystallization from methanol; M.P. 102°–5°, yield: 3.35 g. (82.6%). The IR and NMR spectra were consistent with the structure.

Anal. Calc'd. for $C_{19}H_{20}F_3NO_3$ (percent): C, 62.12; H, 5.49; N, 3.82. Found (percent): C, 62.07; H, 5.38; N, 3.73.

EXAMPLE 13

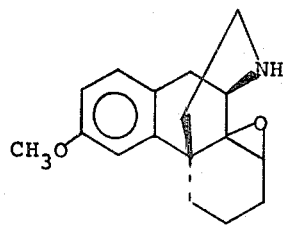

8,14-epoxy-3-methoxymorphinan (XXII).

A mixture of 1.0 g. (2.72 mmole) of the epoxide XXI and 0.103 g. (2.72 mmole) of sodium borohydride in 5 ml. of absolute ethanol was refluxed during 5 minutes. After cooling, the reaction mixture was acidified with dilute hydrochloric acid and then extracted with ether. The aqueous layer was separated and made alkaline by the addition of aqueous ammonia and then extracted with methylene chloride. The resulting extracts were dried over Na$_2$SO$_4$ and concentrated in vacuo to yield 800 mg. of an oil (XXII) which was not further purified but used directly in the next transformation. The IR and NMR spectra were consistent with the structure.

EXAMPLE 14

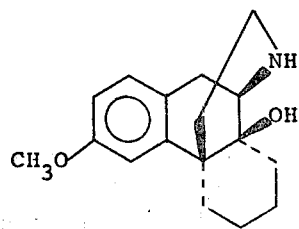

14-hydroxy-3-methoxymorphinan (XXII)

A solution of 800 mg. of the amine-epoxide (XXII) in 10 ml. of tetrahydrofuran was added dropwise at room temperature, to a suspension of 50 mg. of lithium aluminum hydride in 5 ml. of dry tetrahydrofuran. After the addition had been completed, the reaction mixture was stirred and refluxed during fifteen minutes. The excess hydride was destroyed as usual and the solid was filtered off. The filtrate was treated with a saturated solution of hydrochloric acid in ether to yield 720 mg. of a white hydrochloride salt which after recrystallization from methanol melted at 243°–44°C. (dec.). The IR and NMR were consistent with the structure.

Anal. Calc'd. for $C_{15}H_{23}NO_2$. $HCl.\frac{1}{2}CH_3OH$ (percent): S, 64.50; H, 8.04; N, 4.30. Found (percent): C, 64.18; H, 7.81; N, 4.25.

EXAMPLE 15

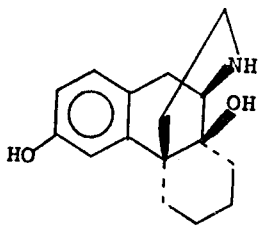

3,14-dihydroxymorphinan (XXIV)

A mixture of 140 mg. (0.5 mmole) of XXIII and 0.55 g. of pyridine hydrochloride was heated under $N_2$ at 185°–95°C. for 1 hour. The mixture was cooled, treated with water and $NH_4OH$ and extracted with $CHCl_3$. The $CHCl_3$ extracts were dried and evaporated to give a solid 53.6 mg. This was treated with ether and filtered. The solid was recrystallized from MeOH to give 50 mg./M.P. 264°–66°C. (d). The IR and NMR spectra were consistent with the structure.

Anal. Calc'd. for $C_{16}H_{21}NO_2$ (percent): C, 74.1; H, 8.16; N, 5.40. Found (percent): C, 73.84; H, 8.35; N, 5.33.

EXAMPLE 16

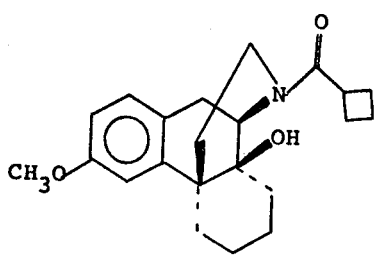

N-cyclobutylcarbonyl-14-hydroxy-3-methoxymorphinan (XXV)

To a stirred and cooled solution of 400 mg. (0.00146 mole) of the amino alcohol XXIII in 0.16 g. (0.002 mole) of dry pyridine and 5 ml. of methylene chloride, there was added, dropwise, a solution of 0.19 g. (0.0016 mole) of the acid chloride of cyclobutyl carboxylic acid in 5 ml. of methylene chloride. After stirring for ten minutes, the reaction mixture washed successively with cold dilute aqueous hydrochloric acid, dilute aqueous sodium hydroxide, water and finally with a saturated aqueous sodium chloride solution. After drying over $Na_2SO_4$ and evaporation of the solvent, there was obtained 400 mg. of an oil which crystallized on standing. The oil was treated with a small amount of cold ether and filtered to yield 320 mg. (61.6%) of crystals which after crystallization from methanol melted at 183°–85°C. The IR and NMR spectra were consistent with the structure.

Anal. Calc'd. for $C_{22}H_{29}NO_3$ (percent): C, 74.33; H, 8.22; N, 3.94. Found (percent): C, 74.19; H, 8.40; N, 3.75.

EXAMPLE 17

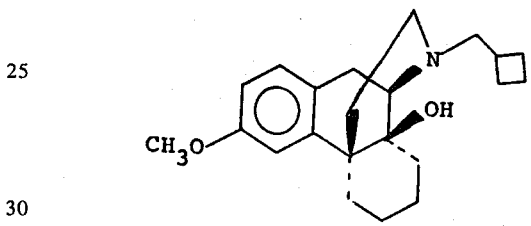

N-cyclobutylmethyl-14-hydroxy-3-methoxymorphinan (XXVI)

To a suspension of 1.0 g. of lithium aluminum hydride in 5 ml. of dry tetrahydrofuran was added at room temperature, under an atmosphere of nitrogen, a solution of 2.14 g. (6 mmole) of the amide XXV in 25 ml. of tetrahydrofuran. The reaction mixture was then refluxed during 30 minutes and worked up as usual to yield 2.0 g. of an oil which was dissolved in ether and the resulting solution filtered through a celite-charcoal mixture.

Treatment with dry HCl gas yielded 2.04 g. of the hydrochloride; M.P. 235°–37° C. (dec.). Recrystallization from methanol increased the melting point to 248°–50° C. (dec.). The IR and NMR spectra were consistent with the structure.

Anal. Calc'd. for $C_{22}H_{31}NO_2.HCl.\frac{1}{2}H_2O$ (percent): C, 68.28; H, 8.60; N, 3.62. Found (percent): C, 68.25; H, 8.40; N, 3.75.

EXAMPLE 18

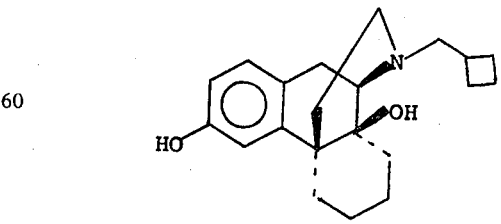

N-cyclobutylmethyl-3,14-dihydroxymorphinan (XXVII)

A mixture of 1.0 g. (2.58 mmole) of XXVI and 10 ml. of 48% HBr was refluxed, under a nitrogen atmosphere, during five minutes. After cooling, the reaction mixture was diluted with water and made basic with aqueous ammonium hydroxide. The aqueous basic mixture was extracted with chloroform and the combined chloroform extracts were dried over anhydrous sodium sulfate. After evaporation of the solvent, the residual oil (730 mg.) was taken up in dry ether and the resulting solution filtered through celite-charcoal. The filtrate was treated with a saturated solution of hydrogen chloride in dry ether. The hydrochloride salt thus obtained was collected by filtration and recrystallized from a methanol-acetone mixture to yield 565 mg. (56.5%) of crystals melting at 272°–74°C. (dec.). The IR and NMR spectra were consistent with the structure.

Anal. Calc'd. for $C_{21}H_{29}NO_2 \cdot HCl \cdot \frac{1}{2}CH_2OH$ (percent): C, 67.97; H, 8.49; N, 3.49. Found (percent): C, 68.10; H, 8.14; N, 3.80.

EXAMPLE 19

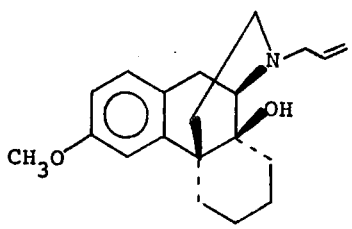

N-allyl-14-hydroxy-3-methoxymorphinan (XXVIII)

To a stirred mixture of 900 mg. (3.3 mmole) of the aminoalcohol XXIII and 1.7 g. (16.5 mmole) of triethylamine in 12 ml. of absolute ethanol was added, at room temperature and under nitrogen, a solution of 0.605 g. (5 mmole) of allyl bromide. After the addition had been completed, the reaction mixture was refluxed for 18 hours and then evaporated to dryness. The residue was mixed with a 20% aqueous sodium carbonate solution and the resulting mixture extracted with several portions of ether. The combined ether extracts were dried over $Na_2SO_4$ and evaporated to yield 940 mg. of an oil which was dissolved in ether. The resulting solution was filtered through a celite-charcoal mixture and the filtrate concentrated at reduced pressure. The remaining oil was converted, in ether, into the hydrochloride salt. Recrystallization from a methanol-ether mixture yielded 600 mg. of a white solid melting at 244°–46° C. (dec.) Yield, 51.9%. The IR and NMR spectra were consistent with the structure.

Anal. Calc'd. for $C_{20}H_{27}NO_2 \cdot HCl$ (percent): C, 68.65; H, 8.07; N, 4.00. Found (percent): C, 68.01; H, 7.97; N, 3.90.

EXAMPLE 20

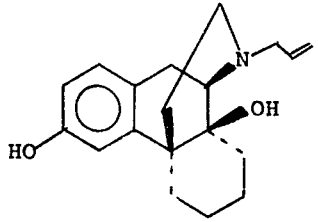

N-allyl-3,14-dihydroxymorphinan (XXIX)

To a solution of 3,814 g. (12.135 mmole) of XXVIII in 90 ml. of dry $CH_2Cl_2$ at −80° C. was added under $N_2$ dropwise a solution of 9.4252 g. (37.42 mmole) of $BBr_3$ of 20 ml. of dry $CH_2Cl_2$. The resulting reaction mixture was allowed to warm up to room temperature slowly for 18 hours. It was decomposed with ice water and the layers separated, the $CH_2Cl_2$ solution washed with water and saturated NaCl solution. It was dried and evaporated to give 3.76 g. of an oil. This was converted to its HCl salt in acetone. The HCl salt obtained was recrystallized from water-acetone to give 1.15 g. of a white solid. The mother liquor was concentrated and converted to its free base. The free base was chromatographed on $Al_2O_3$ (Act. 4) and eluted with $CHCl_3$ to give a fraction (1.35 g.) which was converted to its HCl salt. The HCl salt was recrystallized from $H_2O$-acetone to give 950 mg. The IR and NMR were consistent with the structure. Total yield 2.10 g. (50%).

Anal. Calc'd. for $C_{19}H_{25}NO_2 \cdot HCl \cdot \frac{1}{2}CH_3OH$ (percent): C, 66.56; H, 8.02; N, 3.98. Found (percent): C, 66.65; H, 7.76; N, 3.88.

EXAMPLE 21

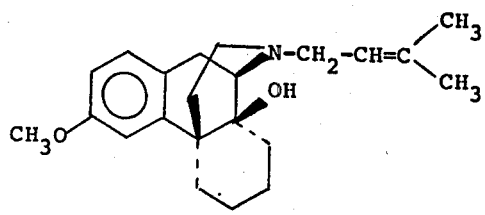

N-dimethylallyl-14-hydroxy-3-methoxymorphinan (XXX)

Substitution in the procedure of Example 19 for the allyl bromide used therein of an equimolar quantity of dimethylallyl bromide produces the title compound.

EXAMPLE 22

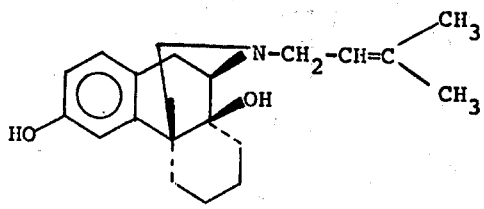

N-dimethylallyl-3,14-dihydroxymorphinan (XXXI)

Substitution in the procedure of Example 20 for the Compound XXIX used therein of an equimolar quantity of Compound XXX produces the title compound

EXAMPLE 23

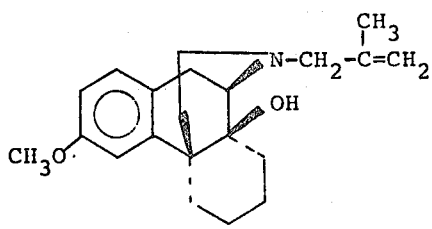

N-2'-methylallyl-4-hydroxy-3-methoxymorphinan (XXXII)

Substitution in the procedure of Example 19 for the allyl bromide used therein of an equimolar quantity of 2-methylallyl bromide produces the title compound.

EXAMPLE 24

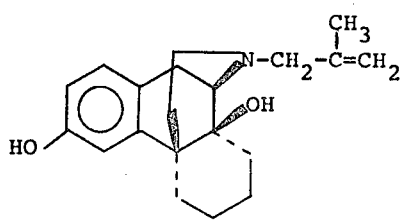

N-2'-methylallyl-3,14-dihydroxymorphinan (XXXIII)

Substitution in the procedure of Example 20 for the Compound XXIX used therein of an equimolar quantity of 2-methylallyl bromide produces the title compound

EXAMPLE 25

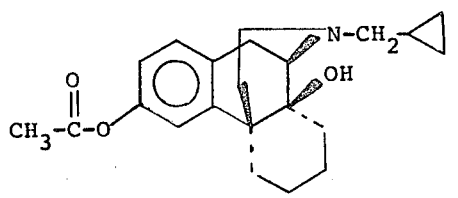

N-cyclopropylmethyl-3-acetoxy-14-hydroxymorphinan (XXXIV)

Equimolar quantities of acetyl chloride, Compound XIX and pyridine are mixed together in dry methylene chloride and the resultant mixture is heated to 60° C. for several hours under a nitrogen atmosphere to produce the title compound.

EXAMPLE 26

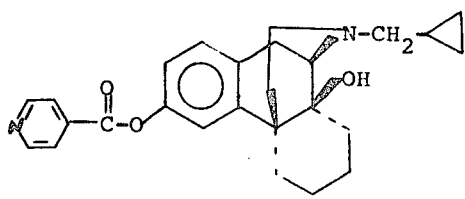

N-cyclopropylmethyl-3-nicotinoyloxy-14-hydroxymorphinan (XXXV)

Equimolar quantities of nicotinoyl chloride hydrochloride, Compound XIX and pyridine are mixed together in dry methylene chloride and the mixture is heated to 50° C. for 3 hours to product the title compound.

EXAMPLE 27

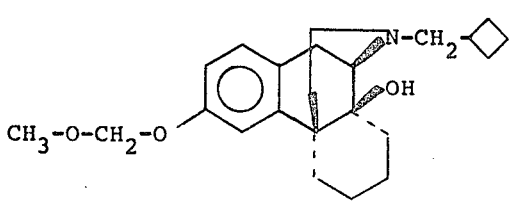

N-cyclobutylmethyl-14-hydroxy-3-methoxymethyloxymorphinan (XXXVI) (XXXVI)

One mole of compound XXVII was placed in 3 liters of benzene. One mole of sodium methoxide was added, followed by the slow addition of 1 mole of chloromethyl ether with stirring. The solution was heated to reflux to yield the title product.

EXAMPLE 28

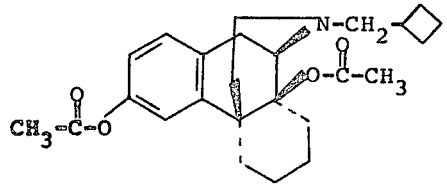

N-cyclobutylmethyl-3,14-diacetoxymorphinan

Two moles each of acetic anhydride and pyridine are mixed with one mole of Compound XXVII in dry methylene chloride. The solution is heated to reflux for 24 hours under nitrogen to produce the title compound.

EXAMPLE 29

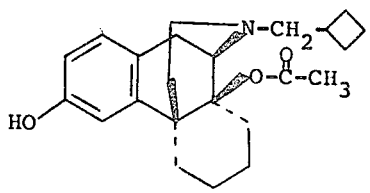

N-cyclobutylmethyl-14-acetoxy-3-hydroxymorphinan (XXXVIII)

One mole of Compound XXXVII is dissolved in excess ethanol. One mole of sodium bicarbonate dissolved in water is added. If necessary, additional ethanol is added to maintain solution. The solution is allowed to stand at room temperature for several days. The solution is concentrated in vacuo at low temperature and then extracted with ether or methylene chloride. The aqueous phase is acidified and extracted with methylene chloride. The title product is isolated from the methylene chloride extract.

EXAMPLE 30

Resolution of dl-3,14-dihydroxy-N-cyclopropylmethylmorphinan into its d and l optical isomers A. 1-3,14-dihydroxy-N-cyclopropylmethylmorphinan (XIXa)

dl-3,14-dihydroxy-N-cyclopropylmethylmorphinan (7.835 g., 25 mmole) as the free base was dissolved in 15 ml. of hot methanol. To this was added a solution of 3.75 g. (25 mmole) of l-tartaric acid in 15 ml. of hot methanol. The resulting solution was diluted with 30 ml. of acetone and let stand at 5° C. for 60 hours to crystallize. It was filtered to yield 3.2 g. of a crystalline solid (A). The mother liquor was evaporated to dryness and was made basic with aqueous ammonia to give approximately 5.0 g. of free base (B).

The solid (A) was recrystallized nine times from methanolacetone to give 500 mg. of the tartrate salt; $[\alpha]D^{22} = -91.26$ (C., 0.4408; CHCl$_3$). This is l-isomer (XIXa).

B. d-3,14-dihydroxy-N-cyclopropylmethylmorphinan (XIXb)

The free base (B), 5.0 g., obtained in Step A above, was dissolved in hot methanol and an equivalent amount of d-tartaric acid dissolved in hot methanol was added. This yielded 5.0 g. of tartrate salt which was recrystallized seven times from methanolacetone; $[\alpha]D^{22} = +63.679$ (C, 0.4028, MeOH).

The tartrate salt was liberated as its free base and recrystallized from CHCl$_3$; M.P. 178°–179°C.; weight 650 mg.; $[\alpha]D^{22} = +91.83°$ C. (C, 0.4168, CHCl$_3$).

This is the d-isomer (XIXb).

EXAMPLE 31

Resolution of the Compounds of the instant invention into their respective optical isomers Substitution into the general procedure of example 30 for the dl-3,14-dihydroxy-N-cyclopropylmethylmorphinan used therein of an equimolar quantity of a dl-3,14-dihydroxy-N-substituted-morphinan will produce the resolved d and l isomers.

EXAMPLE 32

1-3,14-dihydroxy-N-cyclopropylmethylmorphinan pamoate 1-3,14-dihydroxy-N-cyclopropylmethylmorphinan (0.1 mole) is dissolved in hot methanol. A solution of 0.1 mole of pamoic acid dissolved in hot nitrobenzene is added to the first solution with vigorous agitation. The product that crystallizes is the pamoate salt of XIXa.

EXAMPLE 33

Salt preparation of the compounds of the instant invention

Substitution in the procedure of Example 32 for the pamoic acid used therein of an equimolar quantity of sulfuric, nitric, phosphoric, phosphorous, hydrobromic, maleic, malic, ascorbic, citric, tartaric, lauric, stearic, palmitic, oleic, myristic, sulfuric, naphthalenesulfonic, linoleic or linolenic acid produces the corresponding acid addition salt of 1-3,14-dihydroxy-N-cyclopropylmethylmorphinan.

EXAMPLE 34 p-Nitrobenzaldehyde Schiff Base of 4a-(2-aminoethyl)1,2,3,4,4a,9-hexahydro-6-methoxyphenanthrene (Va)

Substitution in the procedure of example 5 for the benzaldehyde used therein of an equimolar quantity of p-nitrobenzaldehyde produces the title product.

EXAMPLE 35 p-Nitrobenzaldehyde Schiff Base of 3-methoxy-9α-bromonorhasubanan

Substitution in the procedure of example 5a for the benzaldehyde Schiff base Va used therein of an equimolar quantity of the p-nitrobenzaldehyde Schiff base produced in example 34 produces the title product.

we claim:

1. The compound having the formula

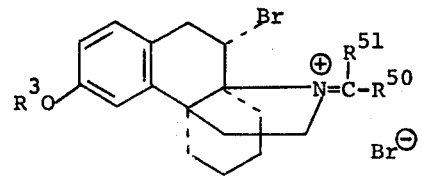

Vb in which R$^3$ is (lower)alkyl, R$^{50}$ is (lower)alkyl or a moiety having the formula

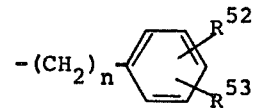

in which n is 0 to 5 inclusive, R$^{52}$ and R$^{53}$ are alike or different and each is H, NO$_2$, Cl, OH, bromo, fluoro, (lower)alkyl or (lower)alkoxy; R$^{51}$ is H, (lower)alkyl or an aralkyl group having the formula

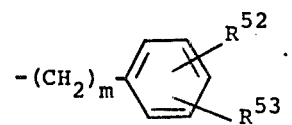

in which m is an integer of 1 to 5 and R$^{52}$ and R$^{53}$ are as defined above.

2. The compound of claim 1 in which R$^3$ is (lower)alkyl, R$^{51}$ is H and R$^{50}$ is phenyl or p-nitrophenyl.

3. The compound of claim 2 in which R$^3$ is methyl.

* * * * *